(12) United States Patent
Stad et al.

(10) Patent No.: US 10,610,369 B2
(45) Date of Patent: Apr. 7, 2020

(54) METHOD OF IMPLANTING A CURABLE IMPLANT MATERIAL

(71) Applicant: DePuy Synthes Products, Inc., Raynham, MA (US)

(72) Inventors: Shawn Stad, Fall River, MA (US); Brooke Mastrorio, Lakeville, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 372 days.

(21) Appl. No.: 14/623,945

(22) Filed: Feb. 17, 2015

(65) Prior Publication Data
US 2015/0157463 A1 Jun. 11, 2015

Related U.S. Application Data

(63) Continuation of application No. 11/608,413, filed on Dec. 8, 2006, now Pat. No. 8,979,931.

(51) Int. Cl.
A61F 2/44 (2006.01)
A61F 2/46 (2006.01)
A61F 2/30 (2006.01)

(52) U.S. Cl.
CPC ............ *A61F 2/441* (2013.01); *A61F 2/4657* (2013.01); *A61F 2/4684* (2013.01); *A61F 2002/3008* (2013.01); *A61F 2002/30062* (2013.01); *A61F 2002/30069* (2013.01); *A61F 2002/30583* (2013.01); *A61F 2002/30586* (2013.01); *A61F 2002/444* (2013.01); *A61F 2002/467* (2013.01); *A61F 2002/4663* (2013.01); *A61F 2210/0004* (2013.01); *A61F 2210/0085* (2013.01); *A61F 2250/0098* (2013.01)

(58) Field of Classification Search
CPC .. A61F 2/44; A61F 2/441; A61F 2/442; A61F 2/4601; A61F 2002/4415; A61F 2002/444; A61F 2002/4435; A61F 2002/448; A61F 2002/4485; A61F 2/4657; A61B 17/1671
See application file for complete search history.

(56) References Cited

U.S. PATENT DOCUMENTS

| | | | |
|---|---|---|---|
| 5,752,971 A | 5/1998 | Rosenbluth | |
| 5,807,327 A | 9/1998 | Green | |
| 5,888,220 A | 3/1999 | Felt | |
| 6,248,110 B1 * | 6/2001 | Reiley | A61B 10/025 606/192 |
| 6,248,131 B1 | 6/2001 | Felt | |
| 6,436,143 B1 | 8/2002 | Ross | |
| 6,733,533 B1 | 5/2004 | Lozier | |
| 6,852,095 B1 | 2/2005 | Ray | |
| 6,958,077 B2 | 10/2005 | Suddaby | |
| 7,291,150 B2 | 11/2007 | Graf | |
| 7,666,205 B2 | 2/2010 | Weikel | |
| 8,221,460 B2 | 7/2012 | Matthews | |

(Continued)

FOREIGN PATENT DOCUMENTS

WO WO 200217825 6/2002
WO WO 2005044154 5/2005

*Primary Examiner* — Kevin T Truong
*Assistant Examiner* — Tracy L Kamikawa
(74) *Attorney, Agent, or Firm* — Nutter McClennen & Fish LLP

(57) ABSTRACT

A method of replacing a nucleus pulposus material wherein curable nucleus pulposus material is injected into a balloon in an intervertebral space 8 Claims, 14 Drawing Sheets

(56) References Cited

U.S. PATENT DOCUMENTS

| | | |
|---|---|---|
| 8,734,459 B1 | 5/2014 | Alobaid |
| 8,979,931 B2 | 3/2015 | Stad |
| 2001/0004710 A1 | 6/2001 | Felt |
| 2003/0195628 A1 | 10/2003 | Bao |
| 2003/0220649 A1 | 11/2003 | Bao |
| 2004/0133280 A1 | 7/2004 | Trieu |
| 2004/0186471 A1 | 9/2004 | Trieu |
| 2004/0230309 A1 | 11/2004 | DiMauro |
| 2005/0027358 A1 | 2/2005 | Suddaby |
| 2005/0065609 A1 | 3/2005 | Wardlaw |
| 2005/0113923 A1 | 5/2005 | Acker |
| 2005/0209601 A1* | 9/2005 | Bowman ............ A61B 17/8805 606/90 |
| 2005/0209602 A1 | 9/2005 | Bowman |
| 2005/0245938 A1 | 11/2005 | Kochan |
| 2005/0251259 A1 | 11/2005 | Suddaby |
| 2006/0085069 A1 | 4/2006 | Kim |
| 2006/0085074 A1 | 4/2006 | Raiszadeh |
| 2006/0155379 A1 | 7/2006 | Heneveld |
| 2006/0253198 A1 | 11/2006 | Myint |
| 2006/0253199 A1 | 11/2006 | Lehuec |
| 2006/0253200 A1 | 11/2006 | Bao |
| 2006/0271061 A1 | 11/2006 | Beyar |
| 2006/0293751 A1 | 12/2006 | Lotz |
| 2007/0021835 A1 | 1/2007 | Edidin |
| 2007/0038300 A1 | 2/2007 | Bao |
| 2008/0140201 A1 | 6/2008 | Stad et al. |
| 2009/0054990 A1 | 2/2009 | Myint |
| 2011/0184422 A1 | 7/2011 | Matthews |
| 2011/0196499 A1 | 8/2011 | Boucher |
| 2019/0008648 A1 | 1/2019 | Stad et al. |

\* cited by examiner

METHOD OF IMPLANTING A CURABLE IMPLANT MATERIAL

CONTINUING DATA

This application is a continuation of co-pending U.S. Ser. No. 11/608,413, filed Dec. 8, 2006, (Stad et al.), entitled "Nucleus Replacement Device and Method (Docket DEP5677USNP), the specification of which is incorporated by reference in its entirety.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contained sulfated functional groups that retain water, thereby providing the nucleus pulposus within its cushioning qualities. These nucleus pulposus cells may also secrete small amounts of cytokines as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells to emit larger than normal amounts of the above-mentioned cytokines. In other instances of DDD, genetic factors, such as programmed cell death, or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins.

As DDD progresses, the toxic levels of the cytokines present in the nucleus pulposus begin to degrade the extracellular matrix (in particular, the MMPs (under mediation by the cytokines) begin cleaving the water-retaining portions of the proteoglycans, thereby reducing its water-retaining capabilities). This degradation leads to a less flexible nucleus pulposus, and so changes the load pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

Intervertebral disc degeneration causes a number of clinical problems, including sequelae related to reduced disc height and herniation. In many cases, a simple discectomy can effectively relieve pain, but in time results in further collapse of the disc space because the intervertebral disc can no longer resist body loads the same as a healthy disc. Spine fusion procedures represent another state of the art treatment for disc problems. Fusion generally involves the use of interbody fusion cages and spinal fixation systems to immobilize the fusion site.

In an effort to substantially maintain the patient's range of motion and to reduce tissue damage associated with surgical intervention, the art has considered nucleus pulposus replacement and enhancement devices. Many of these devices are designed to fill at least a portion of the void left by removal of the nucleus pulposus portion of the disc and provide joint flexibility and shock absorption. Some of the nucleus pulposus devices being evaluated are in situ cured (such as in situ cured polyurethane contained within an outer bladder and in situ cured protein polymers). Other devices under evaluation include relatively solid hydrogels (such as hydrogel contained within a UHMWPE pillow and hydrogel balls).

Other intervertebral motion devices include devices having an articulation interface and cushion-type devices.

Both the fusion and motion intradiscal implants require an accurate determination of the cleared disc space for the best performance, mechanical fit and material interdigitation of the device in order to minimize potential device movement and expulsion. Each of the above-noted treatments involving an implant requires a removal of the natural nucleus pulposus from the disc space. This procedure is called a "discectomy".

The ability of a surgeon to accurately determine the position, size and shape of the cleared disc space during discectomy is currently limited by many factors, including the procedure approach, access, location and the size through the annular wall, as well as available intraoperative imaging techniques. Improper location, size or shape of the cleared disc space following discectomy can greatly impact the size, placement and securement of intervertebral devices that are ultimately placed in the disc space, as well as the biomechanical loading of the device and the physiologic response to the device. For example, improper lateral placement of a nucleus pulposus replacement device may cause migration or expulsion of this implant, leading to continued height loss and irritation of neighboring tissues (including nerve roots), thereby creating additional pain or requiring re-operation.

When attempting to replace the nucleus of a damaged disc with a nucleus replacement implant, the surgeon typically desires to attain a number of related goals. First, the surgeon has a desire to adequately fill the disc space following the removal of disc tissue, while avoiding unnecessary damage to the surrounding annulus fibrosus. There is a further desire to intraoperatively visualize the space to be occupied by the nucleus replacement so that the implant may be effectively implanted. Next, there is a desire to avoid expulsation of the implanted device, which may occur either through the port through which the implant is inserted or through natural annular fissures. Lastly, there is a recognition that addition of radio-opaque agents to the implant may have a detrimental effect upon the performance properties of the implant.

It is known in the medical field to deliver a curable material to a surgical site within an expandable device or membrane, such as a balloon. In some embodiments thereof, a curable cement is delivered to a fractured vertebral body in order to strengthen the structure a regain its stability. In the area of nucleus pulposus replacement, it is known to deliver the curable material through a catheter.

For example, U.S. Published Patent Application Number 2005/0027358 ("Suddaby") discloses a nucleus replacement including a distendable sack or balloon which is inflated with a hardenable material and is detached in situ when the injected material has hardened. Suddaby further teaches that two nested balloons may be inserted, and then filled with materials which have different hardnesses when cured, to simulate a natural disc.

U.S. Published Patent Application Number 2005/0245938 ("Kochan") discloses repair of intervertebral discs with a catheter for inserting through a cannula, the catheter having a distal end and a proximal end and a lumen extending longitudinally therethrough. An expandable balloon may optionally be detachably attached to the catheter near the distal end. The proximal end of the catheter is coupled to an injector that holds a supply of a thermoplastic elastomer material at a predetermined elevated temperature sufficiently high to maintain the thermoplastic elastomer at a liquid state. The device allows a thermoplastic elastomer material to be injected into the intervertebral disc space or the articular joint space as a replacement prosthetic for the disc's nucleus pulposus.

U.S. Published Patent Application Number 2005/0251259 discloses a system for replacing a natural vertebral disc with a synthetic disc, said system comprising an outer balloon adapted to be inserted into an intervertebral disc space, an inner balloon which can be inserted within said first balloon, thus defining a chamber between said first balloon and said second balloon, a first hardenable material in liquid form adapted to be injected into said inner balloon, a second hardenable material in liquid form adapted to be injected into said chamber, said first and second materials having different properties when hardened, and means for injecting said materials into said respective balloons while they are disposed within said intervertebral disc space, whereby a synthetic disc having inner and outer portions with different properties can be formed in said intervertebral space.

U.S. Published Patent Application Number 2005/0209602 discloses an apparatus adapted to deliver a flowable biomaterial to an intervertebral disc space, comprising: a reservoir containing the flowable biomaterial fluidly coupled to the intervertebral disc space; at least one sensor adapted to monitor at least one injection condition of the flowable biomaterial; a controller programmed to; monitor the at least one sensor; control the flow of the flowable biomaterial into the intervertebral disc space in accordance with a first operating parameter; controlling the flow of the flowable biomaterial in accordance with a second operating parameter in response to one or more of the injection conditions reaching a threshold level; and maintaining the second operating parameter during at least a portion of the curing of the flowable biomaterial. incorporates sensors into its system.

U.S. Published Patent Application Number 2003/0195628 discloses a method for repairing a damaged or diseased intervertebral disc, the method comprising the steps of: using minimally invasive techniques to remove damaged or diseased nucleus from the disc; providing a mold apparatus comprising a balloon adapted to contain a biomaterial and a delivery cannula adapted to flowably connect a biomaterial source to the balloon; positioning the balloon in the intervertebral disc space using minimally invasive techniques; providing a biomaterial source comprising a plurality of components adapted to be mixed at the time of use to provide a flowable biomaterial and initiate its cure; mixing the biomaterial components; delivering the flowable biomaterial into the balloon using minimally invasive techniques to provide a distraction pressure to the intervertebral disc space; allowing the delivered biomaterial to cure to permit the cannula to be removed and to provide a permanent replacement for the nucleus; and applying mechanical distraction in combination with the pressurized injection of flowable biomaterial to distract the intervertebral disc space.

U.S. Published Patent Application Number 2005/0113923 teaches a method for implanting a spinal disc nucleus pulposus implant, comprising: removing nucleus pulposus tissue from a spinal disc; and injecting a biocompatible material into an intradiscal space; wherein the biocompatible material is injectable into the intradiscal space in a fluid state below physiological temperatures, and is curable by temperature alone via a reversible phase shift to form a gel at physiological temperatures.

U.S. Published Patent Application Number 2005/0065609 discloses a flexible prosthetic cover shaped to form a replacement nucleus pulposus for an intervertebral disc and comprising an aperture for the introduction of filling material therein, and an elongate introducer member configured to pass into the aperture, the cover having a strengthened portion substantially opposite the aperture for engaging the distal end of the member, the strengthened portion and the said distal end being arranged to interlock, for facilitating orientation of the cover.

U.S. Pat. No. 5,888,220 ("Felt I") discloses a nucleus pulposus replacement device comprising an expandable bag into which in-situ curable polyurethane is injected. Felt further discloses that the placement of the bag can be radiographically verified with the use of a C-arm. See also U.S. Pat. No. 6,248,131, U.S. Published Patent Application Nos. US 2003/0220649 ("Felt II") and US 2003/0195628. Felt II discloses some embodiments in which the balloon has metallic wires or other imageable means incorporated into it so that the balloon can be seen under fluoroscopy. Felt discloses that potential imageable materials include any metal, metal alloys, or ceramics that could be combined with a polymer, and that the imageable material can be in the form of wires, a mesh, or particles incorporated into the balloon or on its surface.

Felt does not disclose the use of a radiographic disc space trial balloon that is inflated to verify the size and geometry of the disc space.

SUMMARY OF THE INVENTION

It is an object of the present invention to provide a nucleus replacement that can be delivered through a small portal to the space formerly occupied by the nucleus pulposus. It is another object of the present invention to provide a means by which the surgeon can intraoperatively determine the space being occupied by the nucleus replacement.

The present invention relates to a nucleus pulposus replacement (NPR) delivered by a catheter and held within an expandable device or membrane, such as a balloon. This configuration helps to reduce the potential for expulsion, helps to distribute the stresses caused by delivery of the nucleus replacement, and can provide the surgeon with a means to determine the volume occupied by the nucleus replacement.

The balloon, which could be constructed from a resorbable material, is delivered to the disc space via a catheter. This delivery method helps to minimize the size of the defect made in the annulus fibrosus during the procedure. The catheter is inserted into the nuclear space following the removal of the native nucleus.

In a first embodiment, the balloon has two ports—an inlet port and an outlet port. These ports can be connected to a pressure-measuring device. After the catheter is placed in the intervertebral space, the balloon is filled with a radio-opaque solution until the desired balloon volume is attained. Following this, the nucleus replacement material is fed into the inlet port of the balloon, while the radiopaque agent is allowed to leave via the outlet port. A constant pressure is maintained to ensure that the volume does not change. Once the balloon is completely filled, it (along with its ports) is allowed to sit until the nucleus material is fully cured. Once curing of the curable nucleus replacement material is accomplished, the catheter, the inlet port and the outlet port are removed, and the remaining annular defect can be sealed.

In some preferred embodiments respecting sequential injection of fluids, the procedure is carried out with a single balloon having a single inlet port and a single outlet port. After the balloon is inserted into the disc space, the outlet port of the balloon is blocked. Next, the balloon is filled through the inlet port with a trial fluid, such as radiopaque saline, and the sufficiency of the expanded balloon is then assessed. If the assessment yields a satisfactory determination, then the surgeon simultaneously opens the outlet port and fills the balloon with NPR implant material. The radiopaque saline drains out the outlet port while as the NPR implant material takes its place inside the balloon, thereby producing a replacement implant.

Therefore, in accordance with the present invention, there is provided a method of replacing a nucleus pulposus in an intervertebral disc, comprising the steps of:
  a) removing the nucleus pulposus from the intervertebral disc to create a space,
  b) inserting into the space a balloon having an inlet port and an outlet port,
  c) conducting an amount of a first fluid comprising a radiopaque agent through the inlet port and into the balloon to produce a first pressure in the balloon,
  d) conducting a second fluid comprising a curable nucleus replacement material through the inlet port and into the balloon to displace the first fluid through the outlet port.

In some embodiments having sequential injection of radiopaque and nucleus replacement materials, injection of the radiopaque materials produces a first pressure in the balloon, and the injection of the curable nucleus replacement material is carried out at substantially the same first pressure. In some embodiments thereof, the amount of the radiopaque fluid conducted into the balloon is measured prior to injecting the curable nucleus replacement material. In some embodiments, the surgeon carries out fluoroscopic assessment of the balloon after injecting the radiopaque material and before injecting the curable nucleus replacement material. Preferably, the inlet and outlet ports are removed from the balloon after curing is accomplished.

In addition, rather than filling the balloon with a radio-opaque solution and risking interactions between the trial sizing fluid and the nucleus replacement materials, the balloon could be manufactured with radio-opaque properties. For example, the elastomer component of the balloon could be impregnated with a radiopaque material such as barium sulfate or could be imprinted with tungsten ink. In these embodiments, the initial trialing fill of the radiopaque balloon could be a simple solution such as water or saline.

Another method of controlling the size of the inflated balloon includes the use of a volume control system. This embodiment can utilize syringes that are actuated to eject controlled, discrete amounts of curable nucleus replacement material.

Therefore, in accordance with the present invention, there is provided a method of replacing a nucleus pulposus in an intervertebral disc, comprising the steps of:
  a. removing the nucleus pulposus from the intervertebral disc to create a space,
  b. inserting into the space a balloon having an inlet port and an outlet port,
  c. conducting a first discrete amount of a fluid comprising a curable nucleus replacement material through the inlet port and into the balloon, and
  conducting a second discrete amount of the fluid through the inlet port and into the balloon.

Preferably, conduction of the fluids is accomplished by i) providing a fluid connection between a syringe containing the curable nucleus replacement material and the inlet port of the balloon, and ii) actuating the syringe to inject the fluid through the inlet port and into the balloon. In some embodiments thereof, the syringe is adapted to expel the fluid in discrete amounts. In some embodiments, the syringe has a threaded barrel, and its plunger is threaded and has an enlarged proximal end so that mechanical advantage may be employed. In some embodiments, the syringe contains a ratchet. In some embodiments, prior to conduction of the discrete amounts of curable nucleus replacement material, a fluid comprising a radiopaque material is conducted through the inlet port and into the balloon, and thereafter the balloon is fluoroscopically assessed.

Therefore, in accordance with the present invention, there is provided a device for replacing a nucleus pulposus in an intervertebral disc, comprising:
  a) a catheter having an inlet tube having a proximal end opening and a distal end opening and an outlet tube,
  b) a balloon having an inlet port and an outlet port, wherein the inlet port is connected to the distal end opening of the inlet tube and the outlet port is connected to the outlet tube, and
  c) an injection device containing a curable nucleus replacement material, the injection device connected to the proximal end opening of the inlet tube.

Also in accordance with the present invention, there is provided a device for replacing a nucleus pulposus in an intervertebral disc, comprising;
  a) an inlet catheter having a proximal end opening and a distal end opening,
  b) an outlet catheter,
  c) a balloon having an inlet port and an outlet port, wherein the inlet port is connected to the distal end opening of the inlet catheter and the outlet port is connected to the outlet catheter, and
  d) an injection device containing a curable nucleus replacement material, the injection device connected to the proximal end opening of the inlet catheter.

In another embodiment of the present invention, two separate, adjacent balloons are employed. A first trial balloon is filled to occupy the disc space, and the appropriate volume is determined thereby. Following this measurement step, this first trial balloon is deflated as the second implant balloon is filled with nucleus replacement material. This second filling is conducted in a manner that will substantially maintain the volume obtained during the filling of the first balloon.

Therefore, in accordance with the present invention, there is provided a method of replacing a nucleus pulposus in an intervertebral disc, comprising the steps of:
  a) removing the nucleus pulposus from the intervertebral disc to create a space,
  b) inserting into the space a first balloon having an inlet port and an outlet port and a second balloon having an inlet port and an outlet port,
  c) conducting a first fluid comprising a radiopaque agent through the inlet port and into the first balloon to substantially fill the space, and d) conducting a second fluid comprising a nucleus replacement material into the second balloon to displace the first fluid through the outlet port of the first balloon.

Preferably, conduction of the curable nucleus replacement material into the second implant balloon is carried out at substantially the same pressure produced in the first trial balloon by conduction of the fluid comprising the radiopaque material.

Preferably, the amount of the radiopaque fluid conducted into the first trial balloon is measured prior to conducting the fluid comprising the curable nucleus replacement material into the second trial balloon. Alternatively, the first trial balloon injected with the radiopaque material is fluoroscopically assessed.

After the fluid comprising the curable nucleus replacement material fills the second implant balloon, it is allowed to cure. Then, the inlet and outlet ports are removed from the balloons.

DETAILED DESCRIPTION OF THE INVENTION

For the purposes of the present invention, a "discectomy" involves the removal of at least a portion of the nucleus pulposus of a degenerated disc. Often, the entire nucleus pulposus is removed. Frequently, a small amount of tissue from the annulus fibrosus portion of the intervertebral disc is removed as well, thereby leaving a central disc space surrounded by the remaining portion of the annulus fibrosus.

Figure 1:
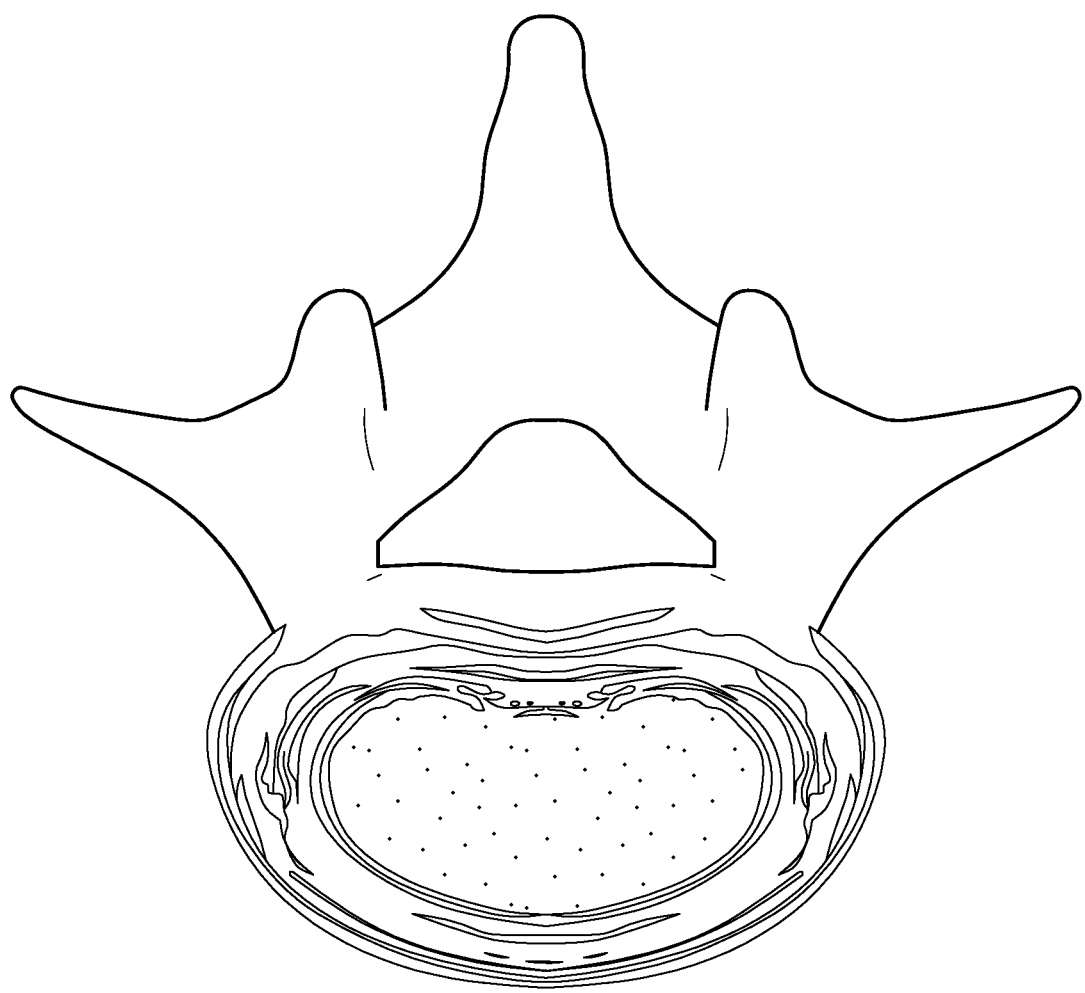
FIG. 1 discloses a cross-section of a damaged intervertebral disc.

FIG. 1 discloses a cross section of a damaged intervertebral disc.

Figure 2:
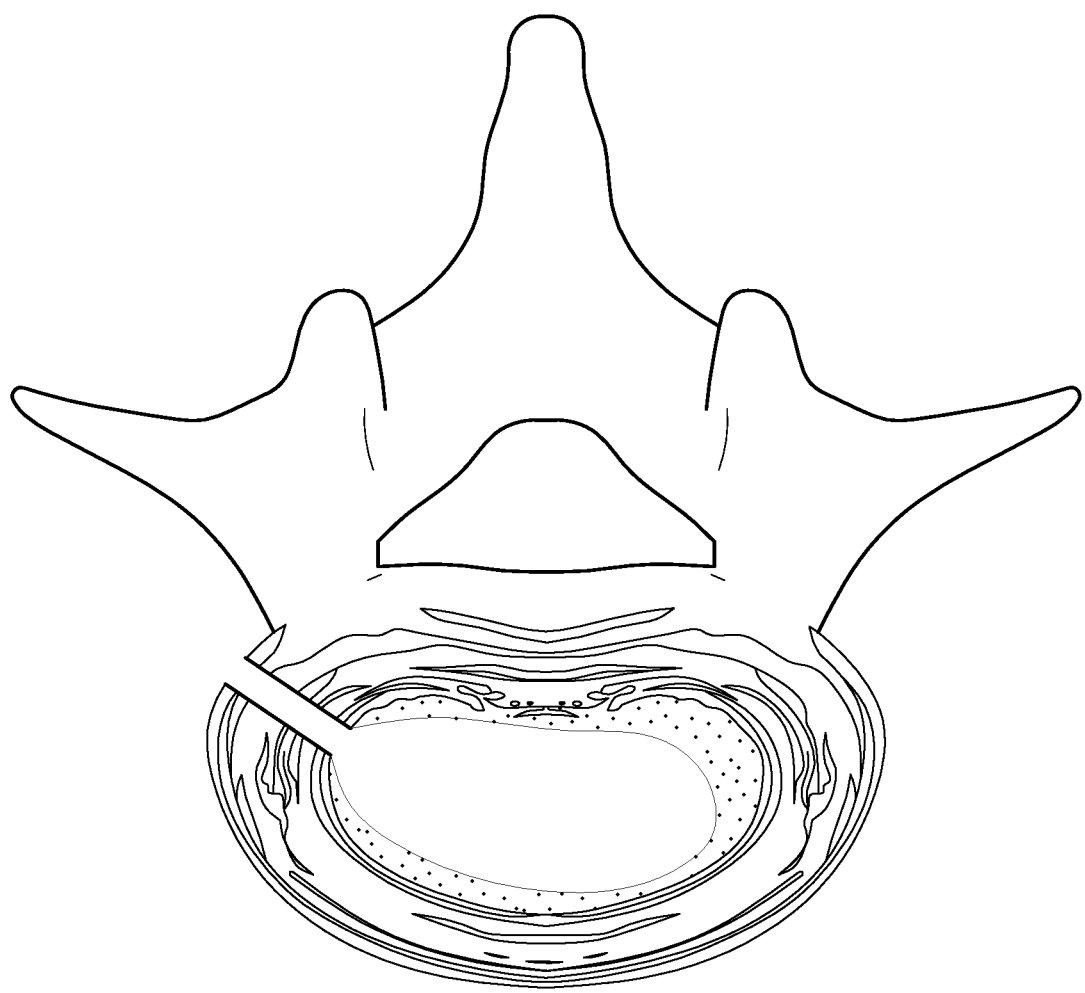
FIG. 2 discloses a cross-section of an intervertebral disc having a majority of the nucleus pulposus removed.
Figure 3:
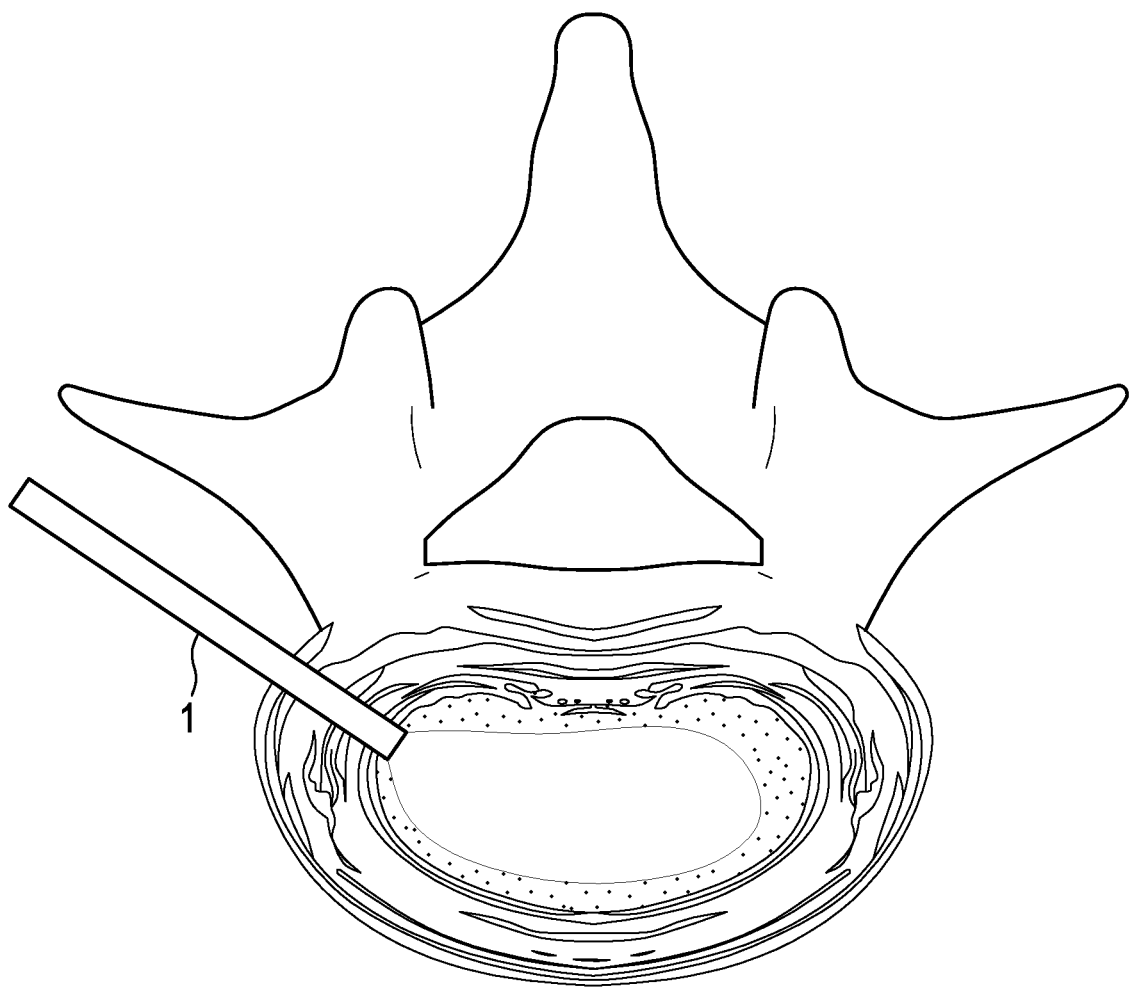
FIG. 3 discloses a cannula inserted into the disc of FIG. 2 through a hole in the annulus fibrosus.

In performing a preferred method of the present invention, first, a discectomy is performed by creating a hole in the annulus fibrosus of the degenerating disc, inserting a tissue removal instrument (such as rongeurs) into the hole, and removing nucleus pulposus tissue from the central portion of the disc. The resulting structure is that shown in FIG. 2, wherein a portion of the nucleus pulposus is removed. Now referring to FIG. 3, a cannula 1 is inserted into the hole in the annulus fibrosus.

In some embodiments, the device comprises a single balloon.

Figure 4:
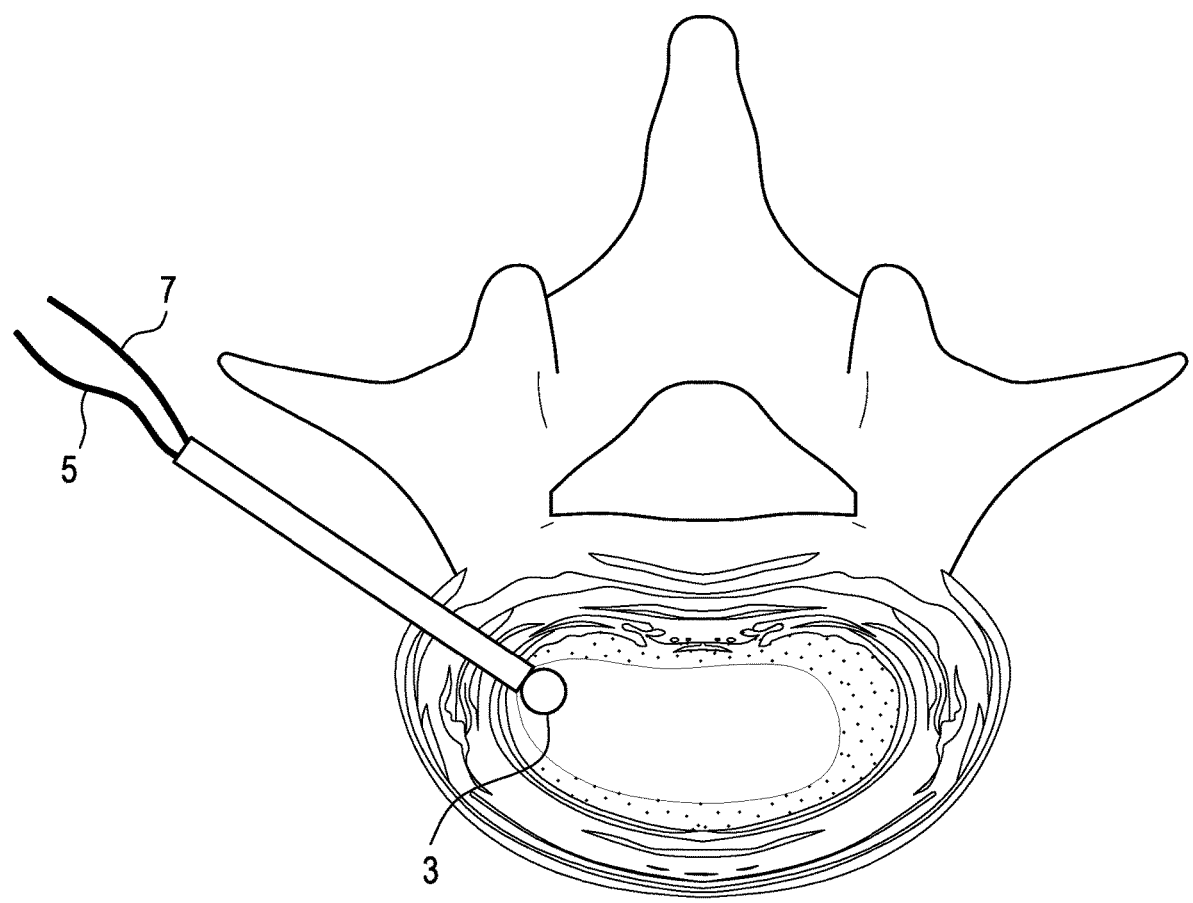
FIG. 4 discloses a single balloon inserted into the disc of FIG. 3 through the cannula.
Figure 5:
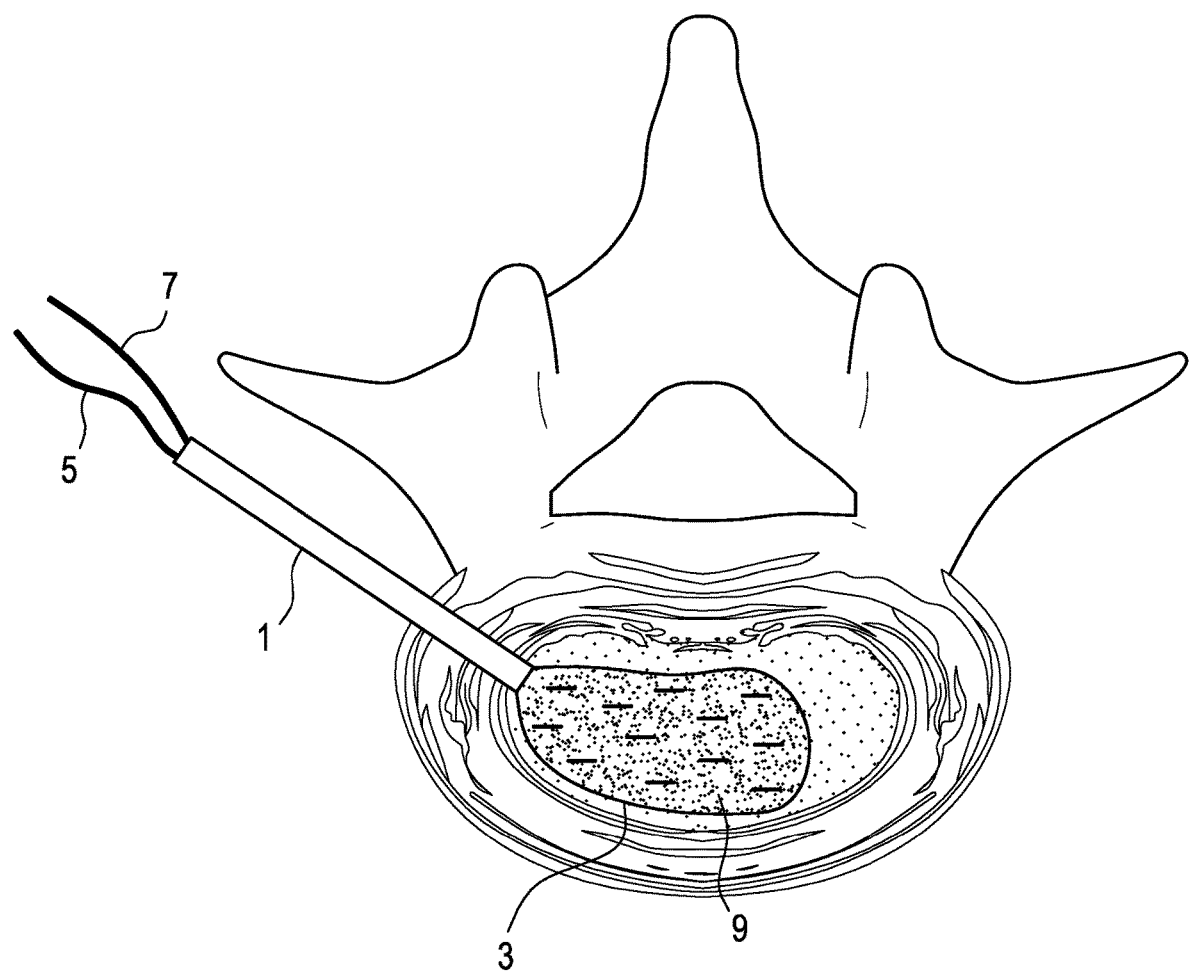
FIG. 5 discloses filling the balloon of FIG. 4 with a radiopaque agent.
Figure 6:
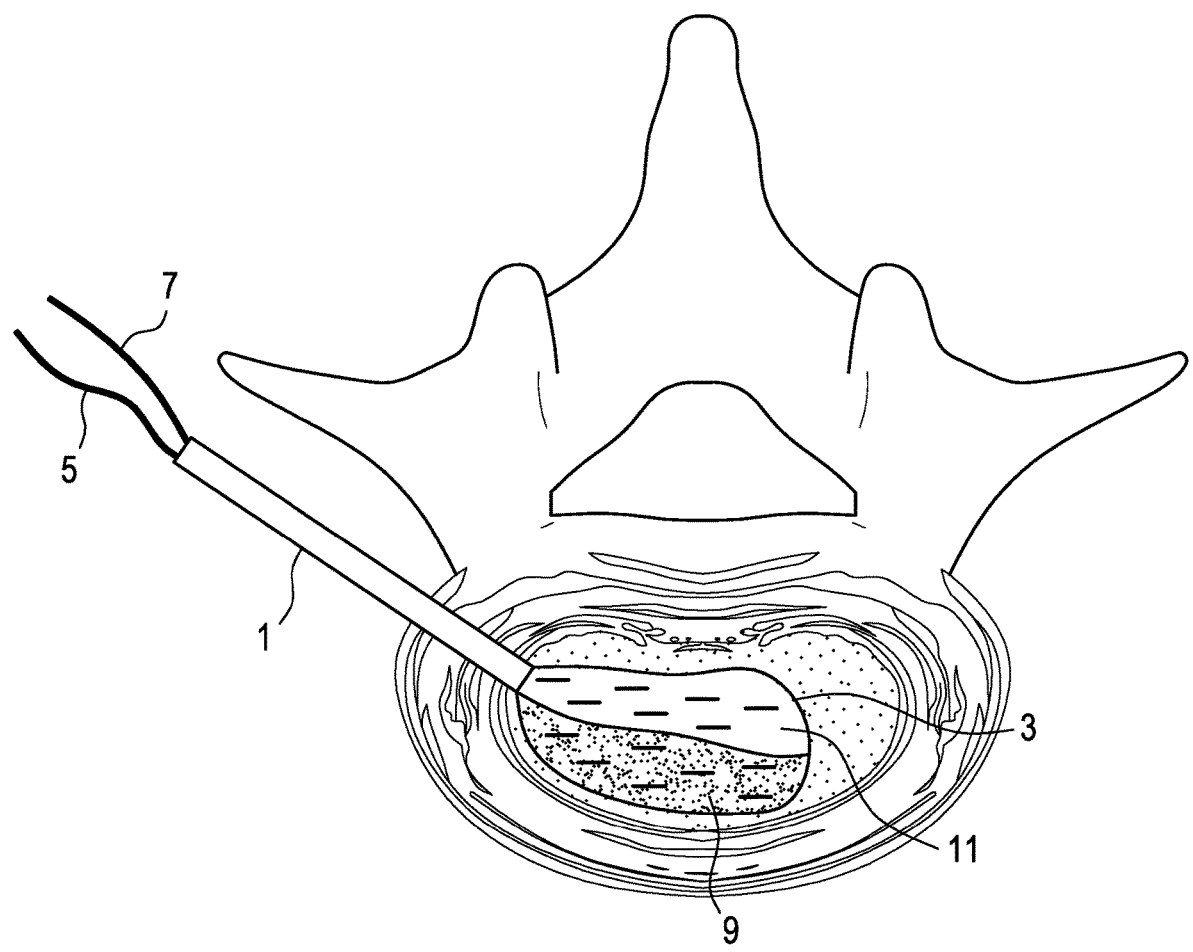
FIG. 6 discloses displacing the radiopaque agent of FIG. 5 with a nucleus replacement material.
Figure 7:
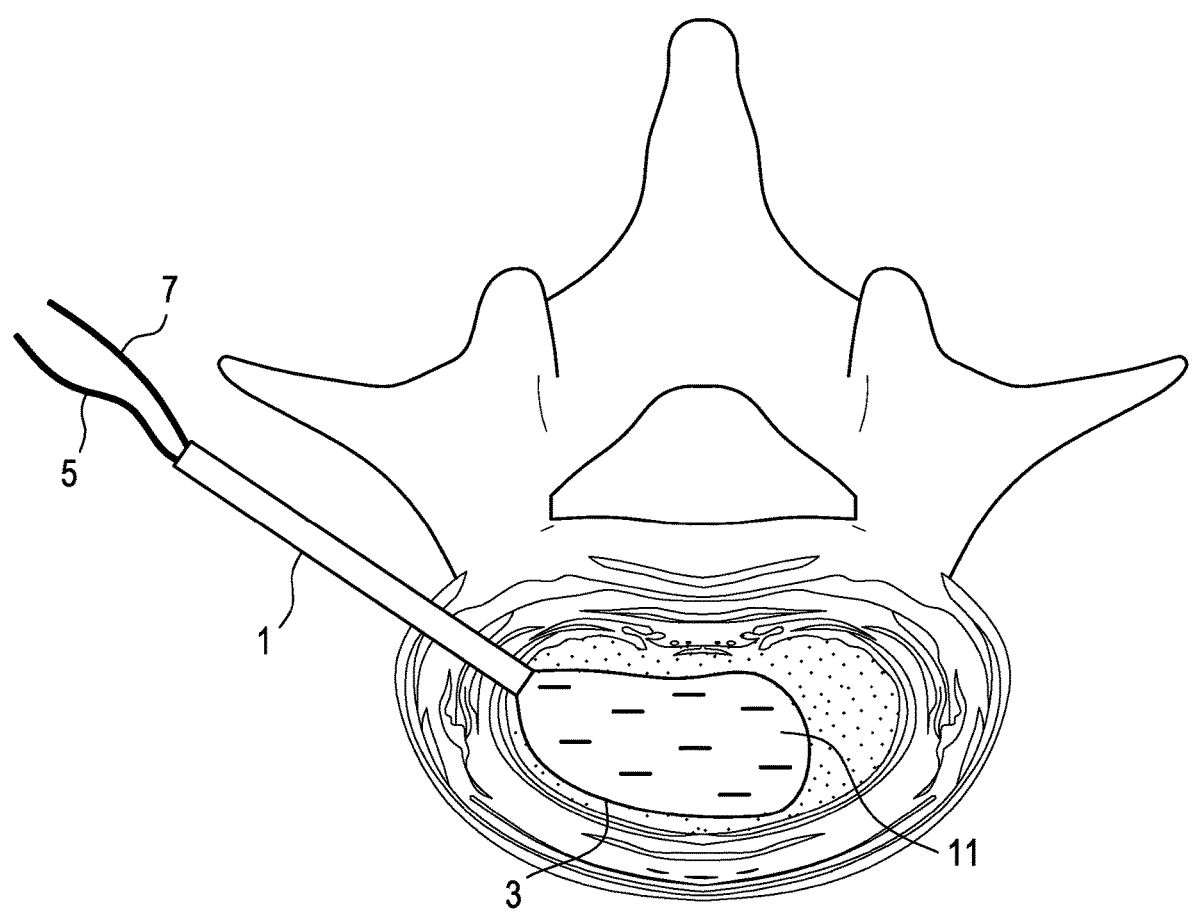
FIG. 7 discloses the balloon of FIG. 6 completely filled with nucleus replacement material.
Figure 8:
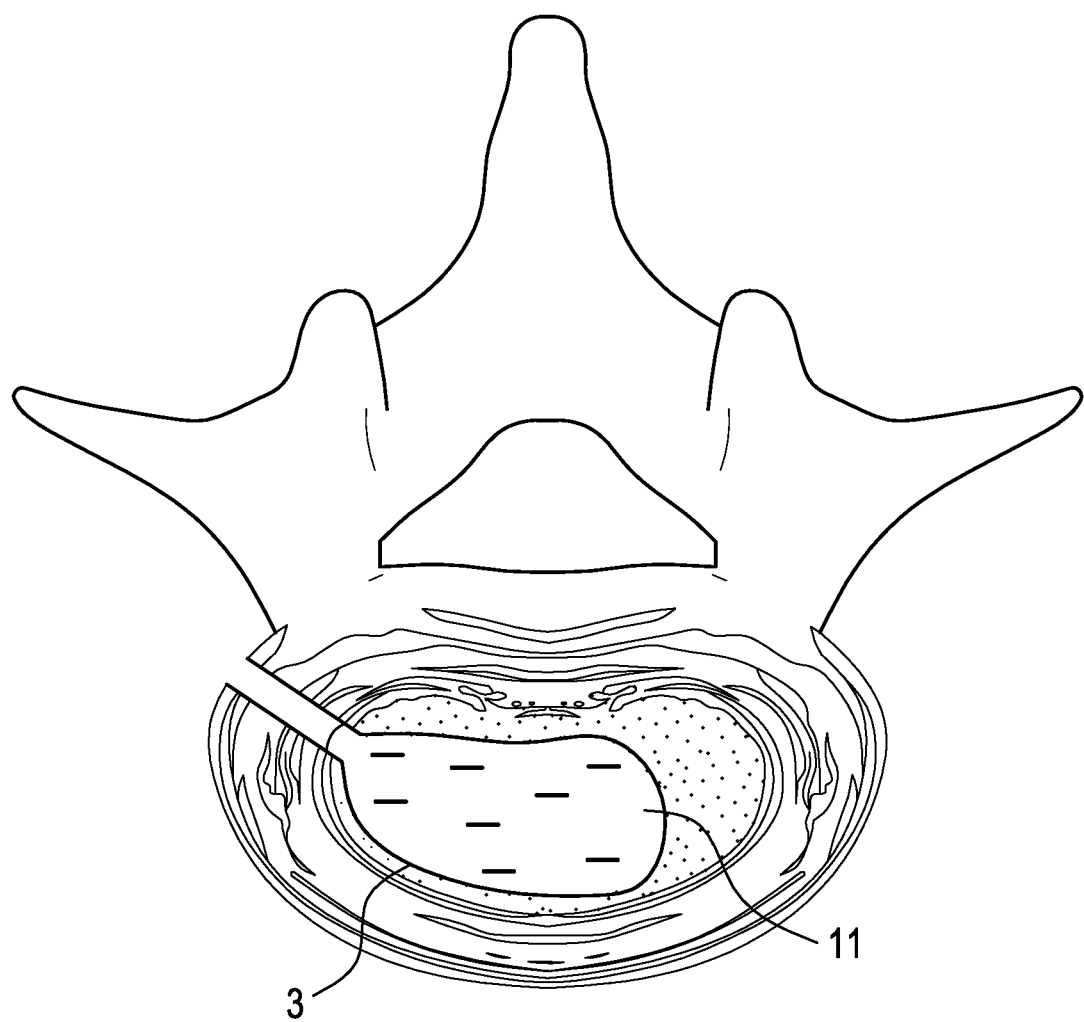
FIG. 8 discloses the balloon of FIG. 7 having its ports removed.

Now referring to FIG. 4, the single balloon device of the present invention is inserted into the cannula. The device comprises a balloon 3 having an inlet port 5 and a outlet port 7. Now referring to FIG. 5, trial material 9 is flowed through the inlet port and into the balloon to fill the balloon with trial material. In one embodiment, the trial material is saline comprising a radiopaque agent. Now referring to FIG. 6, once the trial material 9 has been used to assess the disc space, the outlet port is opened and nucleus replacement material 11 is flowed into the balloon, thereby displacing the trial material 9. In FIG.6, the nucleus replacement material has displaced about half of the trial material from the balloon. Now referring to FIG. 7, the filling of the balloon with nucleus replacement material continues until the balloon is completely filled with nucleus replacement material. Now referring to FIG. 8, once the balloon is completely filled with nucleus replacement material, the outlet port and the inlet port are removed.

In some embodiments, the device comprises two balloons.

Figure 9:
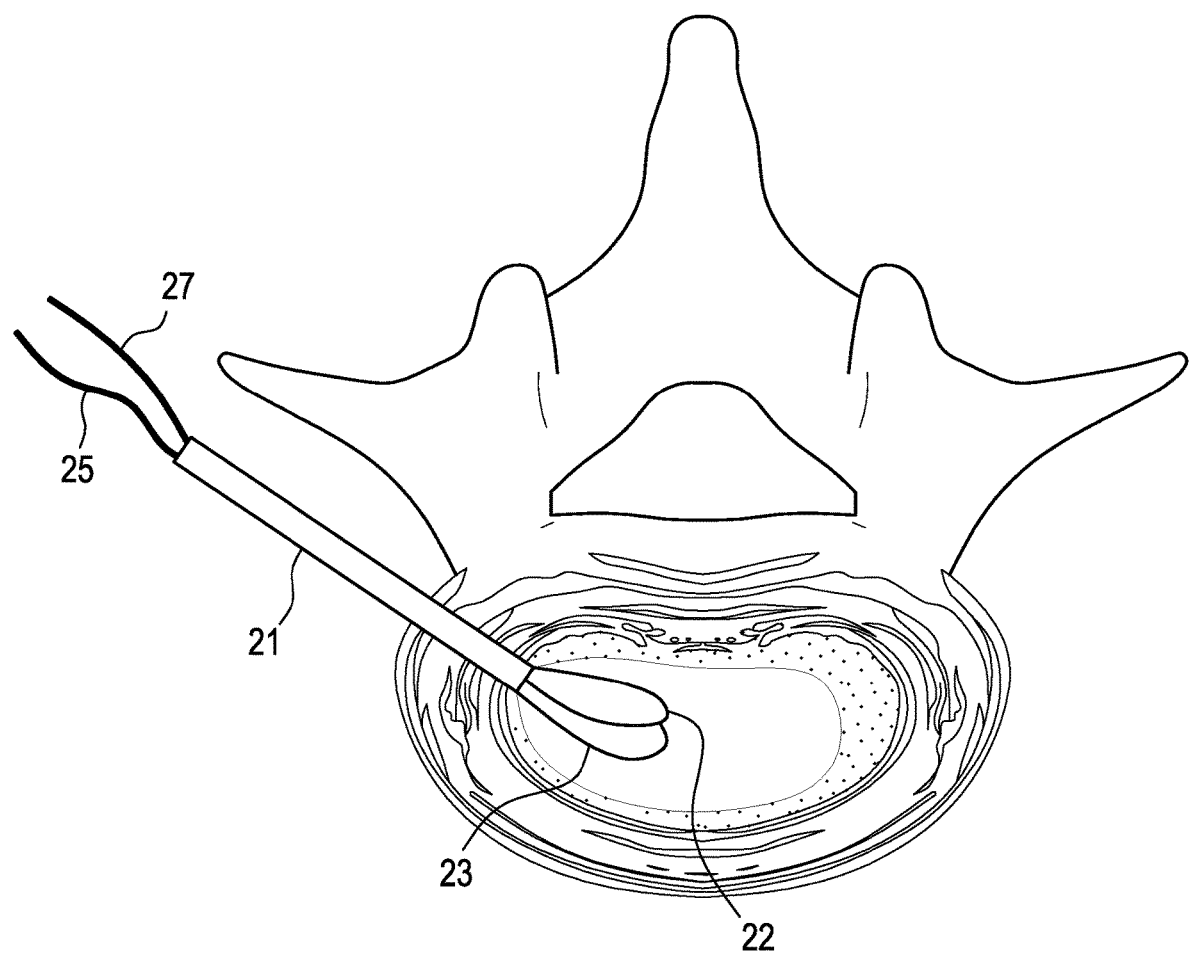
FIG. 9 discloses a dual balloon device inserted into the disc of FIG. 3 through the cannula.

Now referring to FIG. 9, next, the device comprising both a trial balloon and an implant balloon is inserted directly into the disc cavity, preferably by being delivered through a minimally invasive cannula. The inlet and outlet ports for each balloon are shown exiting the cannula.

Figure 10:
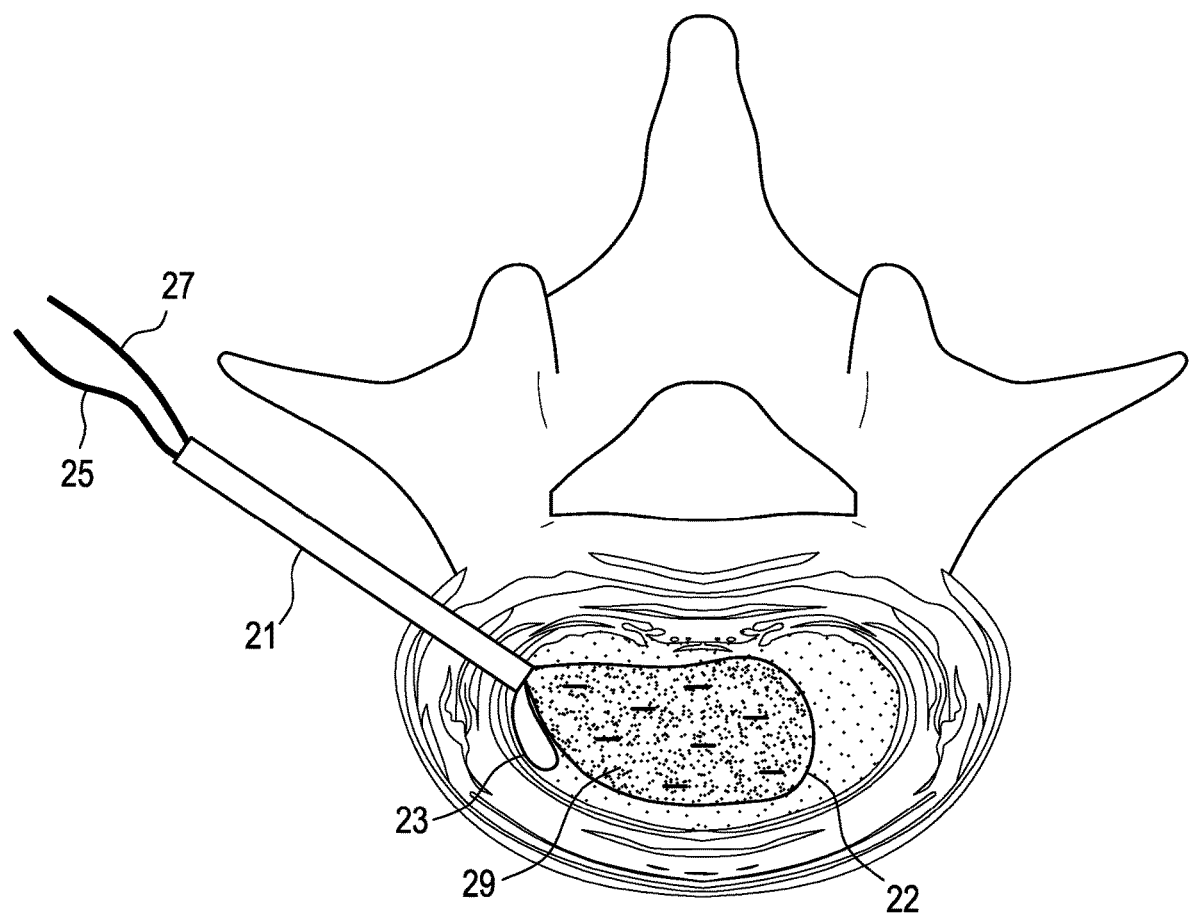
FIG. 10 discloses filling the trial balloon of FIG. 9 with a radiopaque agent.

Now referring to FIG. 10, next, the trial balloon is then inflated to conform to the cleared disc space cavity.

Next, the volume of the intradiscal cavity is obtained by monitoring either the volume of material injected into the balloon, or the pressure in comparison to known balloon expansion values. Intra-operative imaging is then performed to determine the coronal, saggital, and axial placement of the device, as well as the size, angle and geometry of the cleared disc space. The intra-operative imaging may include the use of a C-arm, cineradiography or image guided surgery.

Next, the surgeon makes an intraoperative determination as to whether an adequate intradiscal cavity has been created. If the surgeon determines that the intradiscal cavity is insufficient (for example, the disc space is located to the left of center), the surgeon deflates and removes the device, performs additional discectomy, and then again ascertains the disc space clearance with the trial balloon portion of the device.

Based upon the surgeon's assessment of the amount, size and shape of the disc space cleared, the surgeon can select the appropriate disc treatment procedure, including the injection or insertion of nuclear and annular augmentation materials, disc replacement devices or fusion devices.

Figure 11:
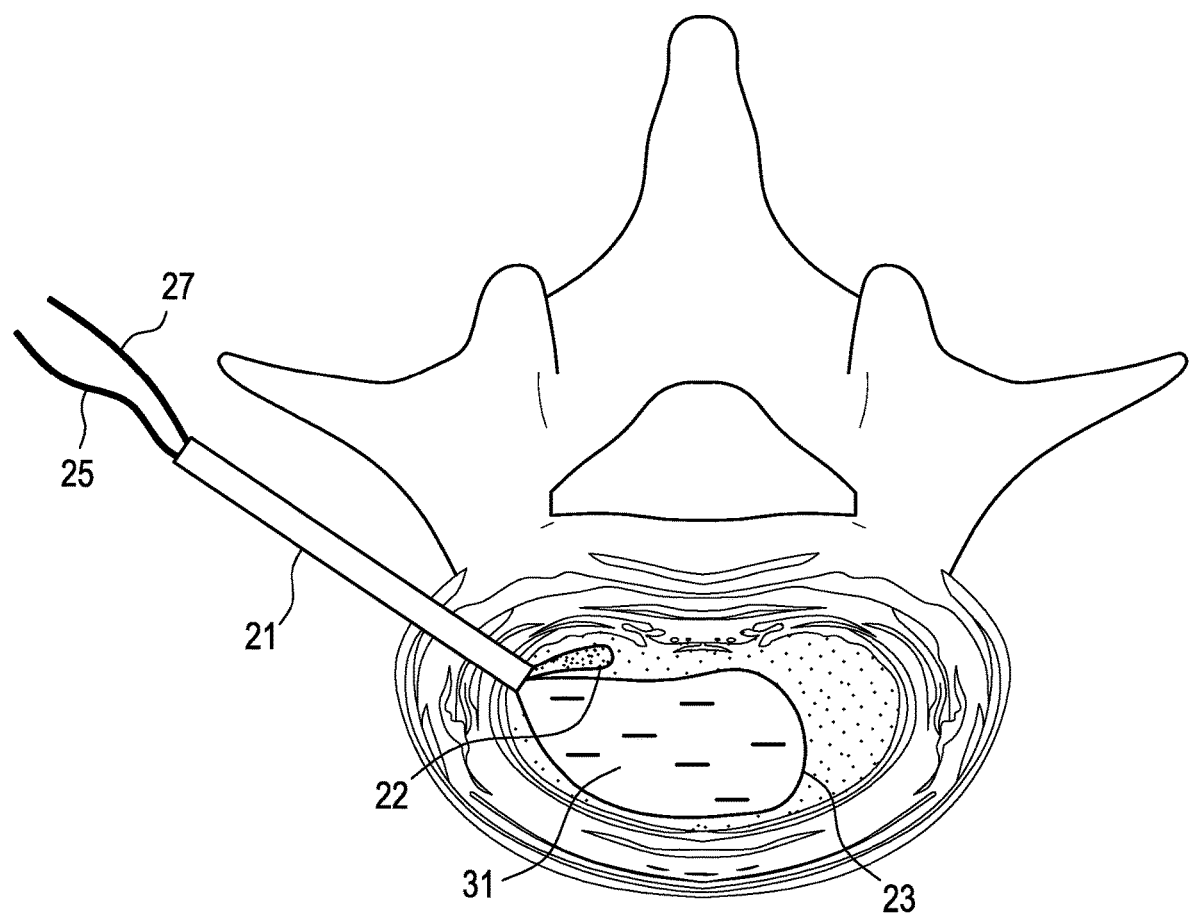
FIG. 11 discloses the implant balloon of FIG. 10 filled with nucleus replacement material and a deflated trial balloon.

Now referring to FIG. 11, if the surgeon decides to replace the nucleus with a nucleus replacement material, the surgeon then fills the implant balloon with a curable nucleus replacement material while deflating the trial balloon. The surgeon then allows the curable material to cure, thereby producing the desired implant.

Therefore, in preferred embodiments, there is provided a method for replacing a nucleus pulposus, comprising the steps of:

a) performing a discectomy to create a disc space;
b) inserting a device comprising a deflated trial balloon and a deflated implant balloon into the disc space;
c) expanding the deflated trial balloon,
d) assessing the disc space via the inflated trial balloon,
e) deflating the trial balloon while inflating the implant balloon with a curable nucleus replacement material; and
f) curing the curable nucleus replacement material.

The above steps will now be discussed in greater detail.

In a preferred embodiment of the present invention, at least a portion of each of the nucleus pulposus and the annulus fibrosus is removed with a disc removal instrument to create a disc space DS. Suitable disc removal instruments include rongeurs, trephines, burrs and curettes. In some embodiments, the method includes removing at least a portion of the nucleus pulposus, wherein the removal step includes creating a vacuum or providing irrigation. In some embodiments, the irrigation is provided by the same cannulated instrument that delivers and expands the balloon. In some embodiments, the method includes removing at least a portion of the nucleus pulposus, wherein the removal step is achieved via chemical dissolution of the nucleus pulposus.

Next, the device comprising the trial balloon and implant balloon is inserted into the disc space in a deflated form. The device comprises:

a) a trial balloon having a lumen and comprising a first expandable material, and
b) a trial tube having a proximal end portion, a distal end portion, and a throughbore (not shown),
c) an implant balloon having a lumen and comprising a second expandable material, and
d) an implant tube having a proximal end portion, a distal end portion, and a throughbore (not shown), wherein the trial balloon lumen is connected to the distal end portion of the trial tube and is in fluid communication with its throughbore, and
wherein the implant balloon lumen is connected to the distal end portion of the implant tube and is in fluid communication with its throughbore.

In some embodiments, and as shown, the device is inserted into the disc space through a cannula. So as to avoid further damage to the annulus, preferably, the cannula is sized to be smaller than the annular opening created in the disc. In other embodiments, the device is inserted without the aid of a cannula.

The balloons can be delivered to the disc space by any suitable means, e.g., in deflated form retained within or upon the end of a rigid or semi-rigid rod or tube.

In some embodiments, the balloons may also be inserted through a hole created in an endplate of an adjacent vertebra above or below the target disc. The balloons may also be inserted into the disc space via a posterior, anterior or anterolateral approach.

Once positioned within the disc space, either centrally within the annular shell or at the edge of the annular rim, a suitable gas (e.g., nitrogen or carbon dioxide), liquid or other flowable expansion medium can be delivered through the tube in order to inflate the trial balloon in situ in a substantially radial, axial and/or longitudinal direction. In some embodiments, beads or other solid media are selected to be the expansion medium and are simply packed into the balloon through the tube.

Next, the trial balloon is expanded while in the disc space. Preferably, the trial balloon is expanded with radio-opaque media (not shown), such as a radio-opaque gas or liquid, or with radio-opaque beads. Once expanded, the trial balloon may be imaged intra-operatively in order to determine the size, shape and location of the disc space. The trial balloon is only partially expanded in the disc space. Preferably, the trial balloon is expanded to completely fill the disc space.

Next, the surgeon makes an intraoperative determination as to whether an adequate intradiscal cavity has been created. In some embodiments, this determination is made by either pressure assessment, fluoroscopic assessment or volumetric assessment. If the surgeon determines that the intradiscal cavity is insufficient (for example, the disc space is located to the left of center), the surgeon deflates and removes the device, performs additional discectomy, and then again ascertains the disc space clearance with the trial balloon portion of the device.

Based upon the surgeon's assessment of the amount, size and shape of the disc space cleared, the surgeon can select the appropriate disc treatment procedure, including the injection or insertion of nuclear and annular augmentation materials, disc replacement devices or fusion devices.

If, through the assessment, the surgeon has decided that sufficient disc space has been cleared, the surgeon then opens the exit port of the trial balloon and deflates the trial balloon (by, for example, providing suction through the exit port) while simultaneously filling the implant balloon with curable implant material. The simultaneously deflation of the trial balloon and inflation of the implant balloon is carried out under constant pressure or volume, so that when the trial balloon is deflated the implant balloon occupies substantially the same space as the trial balloon had occupied. Preferably, the simultaneous deflation/inflation of the balloons is carried out in a manner so as to maintain the disc height spacing created by the trial balloon. In some preferred embodiments, the implant balloon is filled through the injection of a plurality of discrete amounts of curable implant material. The injection of a plurality of discrete amounts of curable implant material allows the surgeon to accurately fill the balloon in a highly controlled manner. Once the implant balloon is completely filled, the cannulae connected with the balloons are removed. Optionally, the trial balloon may be removed as well. The material in the implant balloon is then allowed to cure.

Therefore, in accordance with the present invention, there is provided a device for replacing a nucleus pulposus in an intervertebral disc, comprising;

a) a first catheter having a first inlet tube having a proximal end opening and a distal end opening and a first outlet tube,
b) a first balloon having an inlet port and an outlet port, wherein the inlet port is connected to the distal end opening of the first inlet tube and the outlet port is connected to the first outlet tube, and
c) a first injection device containing a flowable radiopaque material, the first injection device connected to the proximal end opening of the inlet catheter.
d) a second catheter having a second inlet tube having a proximal end opening and a distal end opening and a second outlet tube,
e) a second balloon having an inlet port and an outlet port, wherein the inlet port is connected to the distal end opening of the second inlet tube, and
f) a second injection device containing a curable nucleus replacement material, the injection device connected to the proximal end opening of the second inlet tube.

Also in accordance with the present invention, there is provided a device for device for replacing a nucleus pulposus in an intervertebral disc, comprising;

a) a first inlet catheter having a proximal end opening and a distal end opening, b) a first outlet catheter, c) a first balloon having an inlet port and an outlet port, wherein the inlet port is connected to the distal end opening of the first inlet catheter and the outlet port is connected to the first outlet catheter, and d) a first injection device containing a flowable radiopaque material, the first injection device connected to the proximal end opening of the inlet catheter.

e) a second inlet catheter having a proximal end opening and a distal end opening, f) a second balloon having an inlet port and an outlet port, wherein the inlet port is connected to the distal end opening of the second inlet catheter, and g) a second injection device containing a curable nucleus replacement material, the injection device connected to the proximal end opening of the second inlet catheter.

It may sometimes occur that the surgeon expands the trial balloon and decides that additional height is needed. Therefore, in some embodiment, there is provided a device comprising multiple, vertically arranged balloons. When such a balloon is provided, the surgeon fills the base balloon, and then has the option of filling the superior balloon in order to create more height in the trial or implant balloon. The provision of multiple balloons in the same device avoids the need to replace the undersized balloon and associated catheter with larger ones when the need for additional fill has been determined. In some embodiments, the plurality of balloons may take the form of stacked baffles. In some embodiments, the different balloons within the same disc are provided with different pressures or different compressible materials in order to obtain different properties for different balloons within the same disc. For example, in one embodiments, some but not all of the balloons may be provided with particles that resist shear and dampen axial forces. In some embodiments, the balloons that are closer to the endplates are stiffer than those further away from the endplates. In some embodiments thereof, the stacking could be produced via multiple chambers of the same balloon.

In the lumbar region of the spine, the natural positioning of the vertebral endplates is such that the intervening disc has a wedged shape and provides a lordotic curvature to the spine. Therefore, it would be desirable for the implant balloon of the present invention to expand into a wedged shape that mimics the lordotic curvature of the spine. In other embodiments, the lordotic curvature is attained by implanting at least two balloons in a vertically arranged manner whereby the shape and spatial arrangement of the two balloons form a wedged shape and impart a lordotic curvature to the spine.

Figure 12:
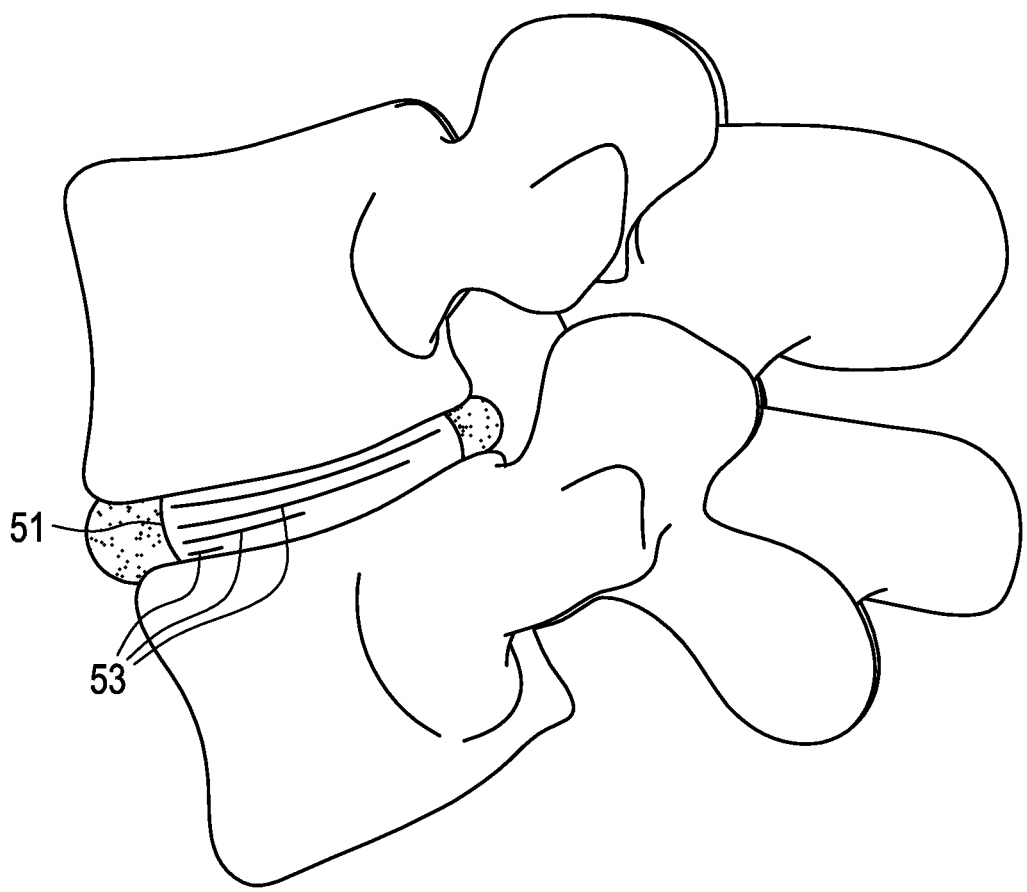
FIG. 12 discloses a side view of a functional spinal unit, wherein the disc space therein has a balloon of the present invention having multiple stacked (empty) chambers.
Figure 13:
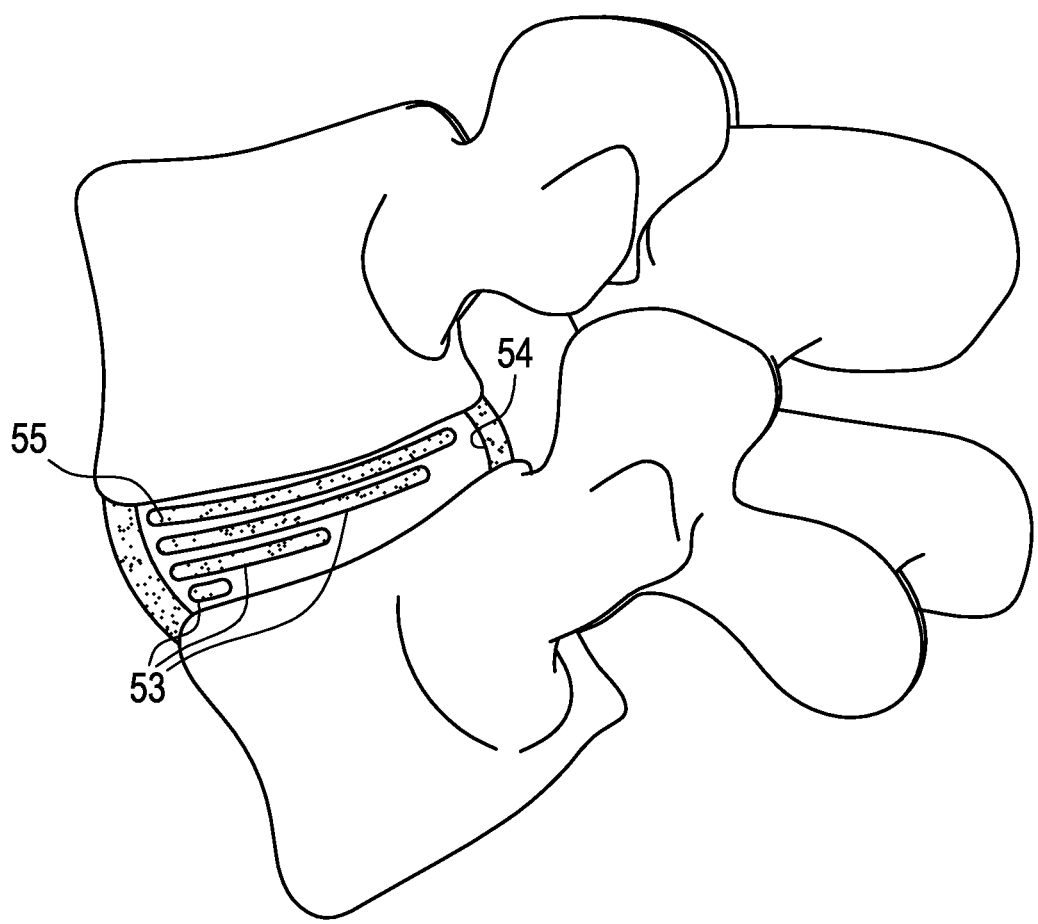
FIG. 13 discloses the balloon of FIG. 12 filled to create the lordosis, wherein the chambers increase in length at higher locations in the disc space.
Figure 14:
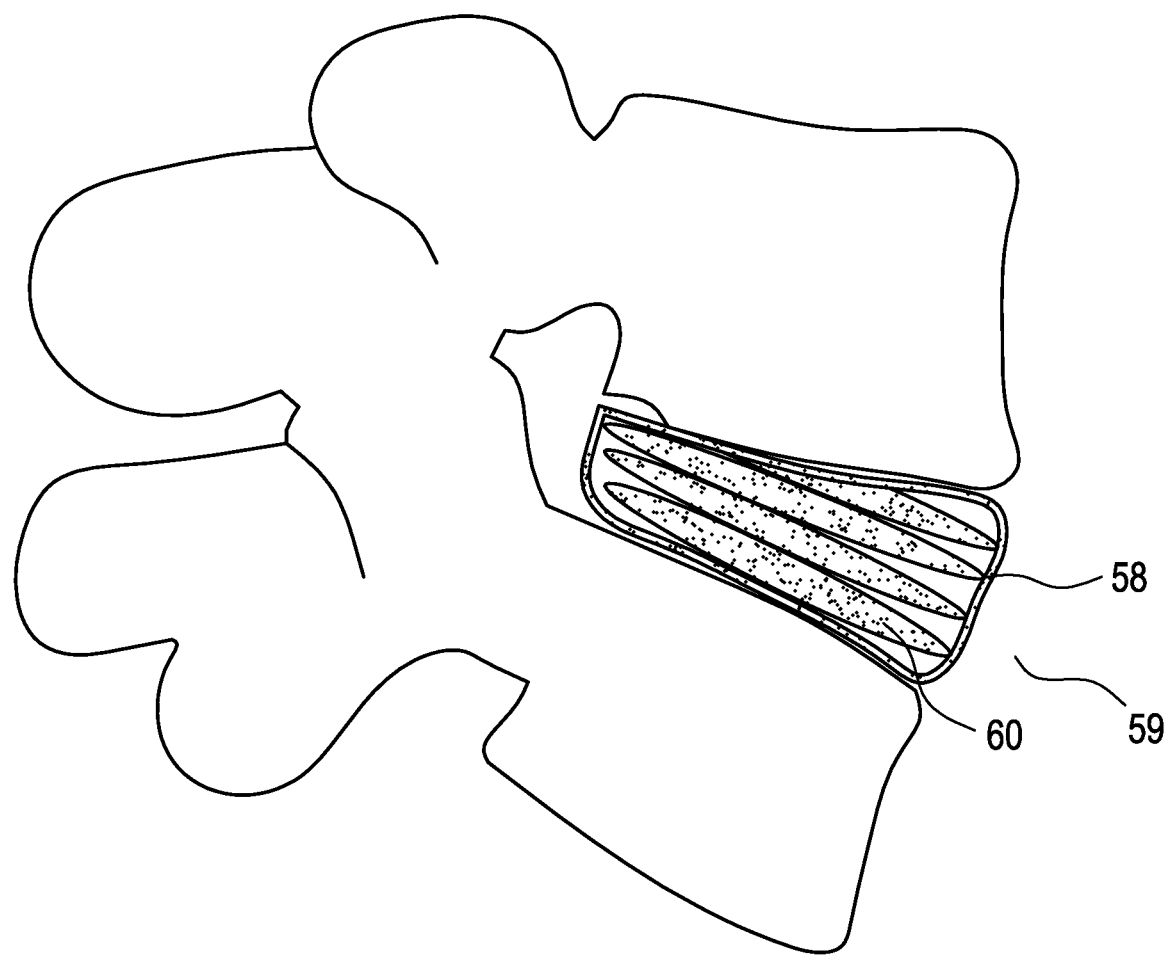
FIG. 14 discloses a side view of a functional spinal unit, wherein the disc space therein has a balloon of the present invention having multiple stacked (filled) chambers to create the lordosis, wherein the chambers increase in length at higher locations in the disc space.

In some embodiments thereof, the lordosis could be produced via multiple chambers of the same balloon. Now referring to FIG. 12, there is provided a balloon of the present invention having multiple stacked (empty) chambers which has been inserted into the disc space. Now referring to FIG. 13, there is provided a balloon of the present invention having multiple stacked chambers which have been filled to create the desired lordosis. In this particular embodiment, the chambers increase in length at higher locations in the disc space. Now referring to FIG. 14, there is provided a balloon of the present invention having multiple stacked chambers which have been filled to create the desired lordosis. In this particular embodiment, the chambers decrease in length at higher locations in the disc space.

In some embodiments, ultrasound is used to assess the shape of the expanded balloon. In these embodiments, the expandable device (such as a balloon) is expanded within the disc space and ultrasound is then used to assess its shape. In some embodiments, the surgeon carries out an ultrasound-based assessment of the balloon after injecting the radiopaque material and before injecting the curable nucleus replacement material. The ultrasound assessment may be carried out with or without the balloon in place. If there is an intact annulus, the balloon may be used to pressurize the voided space and ultrasound may then be used to assess that pressurized space.

Each expandable device or membrane of the present invention (such as a balloon) has at least one lumen, an inside surface, and an outer surface. Also, each balloon has an upper side, a lower side, an anterior side and a posterior side. The trial balloon is typically expanded by passing an expansion medium, such as a fluid or beads, through the lumen to fill the balloon. The implant balloon is typically expanded by filling it with a curable implant material.

Suitable materials for preparing balloons of the present invention may include those that are presently used for such purposes as balloon angioplasty. Suitable materials provide an optimal combination of such properties as compliance, biostability and biocompatability, and mechanical characteristics such as elasticity and strength. Balloons can be provided in any suitable form, including those having a plurality of layers and those having a plurality of compartments when expanded. A useful device will include the balloons, together with a delivery catheter (optionally having a plurality of lumens extending longitudinally therewith), and fluid or gas pressure means.

The balloons are typically made of an expandable material such as a plastic or elastomeric material. Examples thereof include silicone, polyurethane, polyethylene terephthalate, polycarbonate, thermoplastic elastomers and copolymers such as ether-ketone polymers such as poly (etheretherketone). Such polymeric materials can be used in either unsupported form, or in supported form, e.g., by the integration of fibers therein. In addition, the balloons may be made out of any of a wide variety of woven or nonwoven fibers, fabrics, metal mesh such as woven or braided wires, and carbon. Biocompatible fabrics or sheet material such as ePTFE and Dacron™ may also be used.

In a particularly preferred embodiment, the balloons comprise a material selected from the group consisting of polyolefin copolymers, polyethylene, polycarbonate, polyethylene terephthalate, ether-ketone polymers, woven fibers, nonwoven fibers, fabrics and metal mesh.

A radio-opaque material may be mixed with the expandable material to provide a radio-opaque balloon having imaging capability. The radio-opaque material may be provided in the form of a filler, particles, wires or shapes. Suitable radio-opaque materials include barium, barium sulfate, calcium or metallic materials.

The balloons can include markers commonly used in image guided surgery to allow three dimensional reconstruction of the cleared disc space as compared to a preoperatively obtained reconstructed MRI and/or CT. The markers are preferably located upon the outside surface of the balloon. The markers may have spatially varying sizes, shapes or concentrations.

Because volume controlled systems are preferred embodiments of the present invention, in some embodiments, the expandable material of the balloon can be a non-compliant material that expands to a predetermined size. In some preferred embodiments, the distraction of the disc space is accomplished by such an inflatable, rigid (non-compliant) balloon. The non-compliant balloon can be delivered in deflated form to the interior of the annulus and thereafter inflated in order to distract the disc space and provide a spaced region for the delivery of the implant material. The balloon is preferably of sufficient strength and of suitable dimensions to distract the space to a desired extent and to maintain the space in distracted position for a sufficient period of time.

In one embodiment, at least the implant balloon has a wedged shape so that the height of the anterior portion of the expanded device is greater than the height of the posterior portion of the expanded device. This allows the surgeon to restore lordosis when the intervertebral implant is used in either the lumbar or cervical regions of the spine. Preferably, the wedged shape produces an angle of between 5 and 20 degrees, more preferably between 5 and 15 degrees.

In preferred embodiments, the height of the medial portion of at least the implant balloon is greater than the height of either lateral portion of the implant balloon. This geometry more closely mimics the natural doming of the disc space.

In some embodiments, the device can comprise at least one balloon of semicircular, circular, cylindrical, bilateral, or a generally crescent (or banana-like) shape. Upon inflation, each balloon can have a footprint that substantially corresponds to (but is smaller than) a rim of a vertebral endplate, wherein the anterior area height is greater than said posterior area height. More preferably, upon expansion, at least a portion of the balloon has a generally cylindrical shape thereby defining an axial dimension and a radial dimension.

In some preferred embodiments, the balloons may also be used to distract the cleared disc space. When inflated, a non-compliant balloon may provide rigid walls (e.g., when they are fiber-supported or bellows-supported) that are sufficiently strong to distract the space. An inflatable device providing sufficient strength and dimensions for distraction can be prepared using conventional materials. In one embodiment, the uninflated balloon can be delivered to the center of the annular shell, and thereafter inflated to expand the annular shell and in turn, distract the space. Preferably, the expansion medium is injected in an amount sufficient to distract the space.

As used herein, the word "distraction" will refer to the separation of the intervertebral joint surfaces to a desired extent, without rupture of their binding ligaments. Distraction can be accomplished by any suitable means including, for example, hydrostatic means. In one embodiment, the trial balloon is used as a distraction device. By the use of distraction, the disc space can be sufficiently re-established to achieve any desired final dimensions and position. Optionally, and preferably, the means used to accomplish distraction also serves the purpose of forming one or more barriers (e.g., balloons) for the flowable expansion media. If distraction is desired, then the disc space can be distracted prior to and/or during either a discectomy itself and/or delivery of a flowable expansion medium.

A constricted disc space is generally on the order of 3 to 4 mm in height. Suitable distraction means are capable of providing on the order of about 3 atmospheres to about 4 atmospheres, (or on the order of about 40 psi to about 60 psi) of force in order to distract that disc space to on the order of 8 to 12 mm in height. Preferably, when used for distraction, the balloon of the present invention is designed to withstand at least 1 MPa of pressure, more preferably at least 2 MPa, more preferably at least 3 MPa.

Distraction may occur via a multitude of steps or iterations, thereby allowing the soft tissue to relax, thus reducing the risk of soft tissue damage.

Preferably, the expansion media of the in situ formed device can be delivered percutaneously (e.g., through a cannula having a diameter of no more than 6 mm, preferably no more than 2 mm). However, the expansion media of the in-situ formed device can also be delivered in cannulae of much larger dimension (such as up to 18 mm, or through a Craig needle). More preferably, the expansion media of the in-situ formed device is delivered into the disc space in the form of an injectable fluid.

It has been reported in the literature that balloons inserted into the disc space may be subject to retropulsion. Therefore, in some embodiments of the present invention, and particularly those that include distraction, upon expansion, the inflatable implant balloon forms an upper surface having a first plurality of teeth projecting outwards from the upper surface. Upon expansion of the device, these teeth will project in the direction of the upper endplate and, upon complete expansion of the device, will engage the endplate to from a secure interlock with the endplate and resist retropulsion.

In some embodiments, the implant balloon can be coated with an adhesive such as a protein activated sealant, or a sealant that becomes adhesive when wetted or activated.

Preferably, the teeth are made of a stiff non-resorbable material, such as polyetheretherketone (PEEK). Preferably, the teeth have a height of between 0.5 mm and 1.5 mm, and have a triangular cross-section.

In some embodiments of the present invention, upon expansion, the inflatable implant balloon forms an upper surface formed of a material having a high coefficient of friction. Upon expansion of the device, the high coefficient of friction of the upper and lower surfaces will cause a drag upon any movement of the upper surface and therefore keep the device in place and resist retropulsion.

Preferably, the high friction upper and lower surfaces of the implant balloon device are made from a material selected from a group consisting of polyether block copolymer (PEBAX), ABS (acrylonitrile butadiene styrene); ANS (acrylonitrile styrene); Delrin®; PVC (polyvinyl chloride); PEN (polyethylene napthalate); PBT (polybutylene terephthalate); polycarbonate; PEI (polyetherimide); PES (polyether sulfone); PET (polyethylene terephthalate); PETG (polyethylene terephthalate glycol), high and medium melt temperature: polyamides, aromatic polyamides, polyethers, polyesters, Hytrell®, polymethylmethacrylate, polyurethanes: copolymers, EVA (ethylene vinyl acetate) or ethylene vinyl alcohol; low, linear low, medium and high density polyethylenes, latex rubbers, FEP, TFE, PFA, polypropylenes, polyolefins; polysiloxanes, liquid crystal polymers, inomers, Surlins, silicone rubbers, SAN (styrene acrylonitrile), nylons: 6, 6/6, 6/66, 6/9, 6/10, 6/12, 11, all PEBAXs 12; polyether block amides; and thermoplastic elastomers.

Balloons of the present invention can be made using materials and manufacturing techniques used for balloon angioplasty devices. U.S. Pat. No. 5,807,327 ("Green") discloses balloons that may be used in the present invention. The materials disclosed by Green for the formation of the balloon include tough non-compliant layer materials (col. 8, lines 18-36 of Green) and high coefficient of friction layer materials (col. 8, lines 42-54 of Green).

Generally, the balloon is deliverable through a cannula having an inside diameter of between 3 mm and 18 mm, preferably between 4 mm and 12 mm, more preferably between 5 mm and 10 mm.

In some preferred embodiments, a cannula having an inner diameter of no more than 6 mm, is inserted into the disc space.

In some embodiments in which the surgeon desires to minimize the size of the incision, the balloon is preferably deliverable through a cannula having an inside diameter of between 0.5 mm and 6 mm, preferably between 1 mm and 4 mm, more preferably between 2 mm and 3 mm.

In some embodiments, the present invention can be used to provide gradual correction of a scoliotic disc. The degree of curvature can be gradually changes over time by, for example, pumping up the balloons with a syringe.

We claim:

1. A method of replacing a nucleus pulposus in an intervertebral disc, comprising of the steps of:
    a) removing the nucleus pulposus from the intervertebral disc to create a space,
    b) inserting into the space a first balloon comprising an inlet port and an outlet port and a second separate, adjacent balloon comprising an inlet port and an outlet port,
    c) conducting a first fluid comprising a radiopaque agent through the inlet port of the first balloon and into the first balloon to substantially fill the space, and
    d) conducting a second fluid comprising a curable implant material into the second balloon to inflate the second balloon and displace the first fluid through the outlet port of the first balloon to provide simultaneous deflation of the first balloon and inflation of the second balloon carried out under substantially constant pressure,
    wherein the first and second balloons are laterally disposed beside each other during step b).

2. The method of claim 1 wherein the amount of the first fluid conducted into the first balloon is measured prior to step d).

3. The method of claim 1 further comprising:
    e) curing the implant material.

4. The method of claim 3 wherein the inlet and outlet ports are removed from the second balloon after step e).

5. The method of claim 1 further comprising the step, between steps c) and d), of:
    e) fluoroscopically assessing the first balloon.

6. The method of claim 1, wherein an outer surface of the first balloon abuts the space.

7. The method of claim 1, wherein an outer surface of each of the first balloon and the second balloon abuts the space.

8. A method of replacing a nucleus pulposus in an intervertebral disc, comprising the steps of:
    a) removing the nucleus pulposus from the intervertebral disc to create a space,
    b) inserting into the space a first balloon comprising an inlet port and an outlet port and a second separate, laterally adjacent balloon comprising an inlet port and an outlet port,
    c) conducting a first fluid comprising a radiopaque agent through the inlet port of the first balloon and into the first balloon to substantially fill the space, and
    d) conducting a second fluid comprising a curable implant material into the second balloon to displace the first fluid through the outlet port of the first balloon,
    wherein the simultaneous deflation of the first balloon and inflation of the second balloon is carried out under substantially constant pressure, so that when the first balloon is deflated the second balloon occupies substantially the same space as the first balloon had occupied, so that the simultaneous deflation/inflation of the balloons is carried out in a manner so as to maintain a disc height spacing created by the first balloon.

* * * * *